United States Patent
Brocia

(10) Patent No.: US 10,842,841 B2
(45) Date of Patent: Nov. 24, 2020

(54) METHOD FOR ISOLATION OF MAO INHIBITORS FROM TEQUILA OR OTHER DISTILLED AGAVE FERMENTATION PRODUCTS

(71) Applicant: Roar Holding LLC, New York, NY (US)

(72) Inventor: Robert W. Brocia, Bronxville, NY (US)

(73) Assignee: Roar Holding LLC, New York, NY (US)

(*) Notice: Subject to any disclaimer, the term of this patent is extended or adjusted under 35 U.S.C. 154(b) by 65 days.

(21) Appl. No.: 15/946,656

(22) Filed: Apr. 5, 2018

(65) Prior Publication Data

US 2018/0296629 A1    Oct. 18, 2018

Related U.S. Application Data

(60) Provisional application No. 62/601,946, filed on Apr. 5, 2017.

(51) Int. Cl.
| | | |
|---|---|---|
| *A61K 36/00* | (2006.01) | |
| *A61K 36/88* | (2006.01) | |
| *A61P 25/16* | (2006.01) | |
| *A61P 25/24* | (2006.01) | |
| *A23L 2/52* | (2006.01) | |
| *A23L 33/105* | (2016.01) | |
| *C12H 3/04* | (2019.01) | |

(52) U.S. Cl.
CPC .............. *A61K 36/88* (2013.01); *A23L 2/52* (2013.01); *A23L 33/105* (2016.08); *A61P 25/16* (2018.01); *A61P 25/24* (2018.01); *A61K 2236/39* (2013.01); *A61K 2236/51* (2013.01); *C12H 3/04* (2019.02)

(58) Field of Classification Search
None
See application file for complete search history.

(56) References Cited

U.S. PATENT DOCUMENTS

| | | | |
|---|---|---|---|
| 4,612,196 A * | 9/1986 | Goldstein | C12H 3/04 426/14 |
| 10,195,163 B2 * | 2/2019 | Brocia | C12H 3/04 |
| 2013/0334115 A1 | 12/2013 | Volker | |
| 2015/0093470 A1 * | 4/2015 | Hobson | A23L 2/84 426/14 |
| 2015/0352173 A1 | 12/2015 | Madhavamenon et al. | |
| 2016/0074343 A1 | 3/2016 | Brocia | |

FOREIGN PATENT DOCUMENTS

WO    WO-2012/128534    9/2012

OTHER PUBLICATIONS

Skaliotis, "Beverage Applications using Spinning Cone Technology," Food Marketing & Technology (2012) Retrieved from the Internet: http://www.harnisch.com/uploads/tx-harnisch/food-03-12-26-28.pdf.

* cited by examiner

*Primary Examiner* — Michael Barker
*Assistant Examiner* — Randall Winston
(74) *Attorney, Agent, or Firm* — Morrison & Foerster LLP

(57) ABSTRACT

Improved compositions of reversible monoamine oxidase inhibitors are obtained by improved methods of alcohol removal from distillates of fermented agave extracts.

5 Claims, 4 Drawing Sheets

METHOD FOR ISOLATION OF MAO INHIBITORS FROM TEQUILA OR OTHER DISTILLED AGAVE FERMENTATION PRODUCTS

CROSS-REFERENCE TO RELATED APPLICATIONS

This application claims priority to U.S. provisional Application No. 62/601,946 filed 5 Apr. 2017. The contents of the above patent application are incorporated by reference herein in their entirety.

TECHNICAL FIELD

The invention is directed to improvements in providing compositions that comprise inhibitors of monoamine oxidase A and monoamine oxidase B (MAO A and MAO B) from distilled spirits derived from agave.

BACKGROUND ART

U.S. Patent Publication 2016/0074343 describes the production of compositions containing significant concentrations of inhibitors of MOA A and MOA B from tequilas and from pulque. Reverse osmosis and spinning column technologies are mentioned as techniques for removing alcohol while preserving the activity of these inhibitors, as these inhibitors are volatile and may be formed during fermentation and distillation of tequila and fermentation of pulque. However, details of these processes are not provided. The present invention provides specifically an improved set of processes for removing ethanol from tequila or other distilled agave fermented extracts while providing a substantially ethanol-free composition with significant concentrations of MAO and/or MAO B inhibition.

As it is known that MAO inhibitors can be used as mood elevators, antidepressants and treatments for various other diseases, including Parkinson's disease, compositions of the invention are useful in these contexts.

DISCLOSURE OF THE INVENTION

The invention takes advantage of the presence of MAO inhibitors in distilled spirits prepared from fermented agave extracts. The MAO inhibitors are formed during fermentation or formed during distillation or aging or combinations of the above. Removing the alcohol from these commercially available spirits by applying a vacuum destroys at least some of the MAO inhibition activity, so the desired compositions must be prepared from these spirits by processes that preserve these volatile components. These processes include reverse osmosis, spinning cone columns, pervaporation and other methods that do not result in the loss of volatile compounds. Particular formats for these processes are shown to have significant advantages.

In one aspect, the invention is directed to improved methods to obtain compositions wherein the activity of inhibitors of monoamine oxidases is preserved but the alcohol content is reduced to less than 1.5% by volume, or 1.0% by volume or 0.5% by volume, often as low as 0.2% by volume or 0.1% by volume, and to compositions obtained by this method. Thus, the invention is directed to a method to improve the isolation of MAO A and/or MAO B inhibitors from a distillate of fermented agave extract by reverse osmosis which method comprises diluting the distillate in a feed reservoir of a reverse osmosis system and recycling said diluted distillate across a separation membrane to obtain a permeate and a concentrate that is returned to the feed reservoir at each cycle; and continuing to recycle each successive concentrate to obtain a final concentrate that contains less than 1.5% alcohol by volume (ABV), thus obtaining an improved composition of said inhibitors.

The invention is also directed to a composition comprising inhibitors of MAO A and/MAO B obtained by the improved process of the invention or composition comprising inhibitors of MAO A and/or MAO B derived from the distillate of a fermented agave extract which contains less than 1.5% ABV or 1.0% ABV or 0.5% ABV or even less as noted above. The invention also is directed to foodstuffs or drinks that contain these compositions and to methods to treat conditions requiring MAO inhibition using any of these. As it has been found that the MAO inhibitors in the invention compositions are reversible, these are particularly useful for treatment in subjects who are intolerant to irreversible MAO inhibitors.

MODES OF CARRYING OUT THE INVENTION

Figure 1:
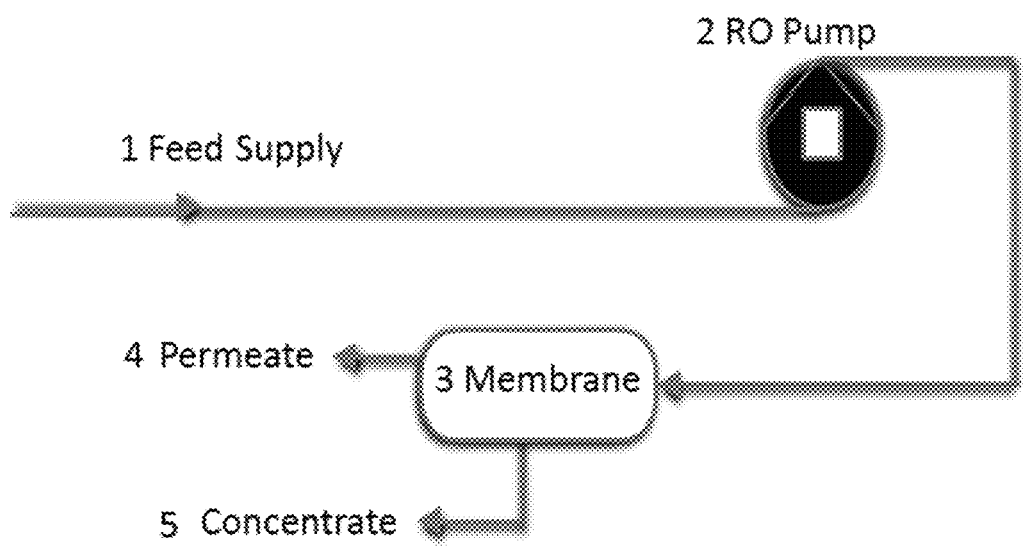
FIG. 1 shows a conventional reverse osmosis process generally designed so that the permeate is retained, in the case, for example, of the purification of brackish or sea water.

In one embodiment, the agave derived alcoholic beverage has been prepared by heating the stems of agave cactus to hydrolyze complex sugars; shredding and crushing the heated stems to release a syrup; diluting said syrup with water to a 12-14 BRIX level and inoculating with yeast; fermenting the inoculated diluted syrup to obtain a fermentation product; and distilling the fermentation product to obtain a distillate.

Alternatively, the distillate is prepared from a species of agave that does not require processes to break down complex sugars, such as an extract of the maguey plant used to make pulque.

In all cases, a distillate of a fermented extract of an agave plant is treated to remove alcohol in a process that does not also remove the MAO inhibitors, which inhibitors are also volatile compounds.

One successful method to remove the ethanol from the beverage starting material is reverse osmosis (RO). An RO membrane with a molecular weight cut-off of approximately 100 Daltons, i.e., 90-110 Daltons separates ethanol from the inhibitors of MAO's formed by microorganisms and/or formed during distillation.

In some embodiments, in the improved method of the invention, reverse osmosis (RO) with dilution and subsequent circulation are continued until the product is considered nonalcoholic. Additional pressure adjustments with respect to the flow over the separation membrane may also be required and supplied by use of additional pumps, valves and gauges. The active MAO inhibitors are then contained in the concentrated, non-alcoholic portion and may then be supplemented with vitamins, minerals, amino acids, protein or caffeine, where desired, and may be included in other food or drink preparations as noted above. The alcohol content is reduced to less than 1.5% by volume or 1.0% by volume, but may be reduced even further. Illustrative descriptions of this process are provided in the examples below.

As noted above, the MAO inhibitors produced in fermented agave sources are volatile compounds that typically follow ethanol through evaporative separation techniques. The compounds are selective inhibitors of MAO A or MAO B and the ratio of MAO A:MAO B inhibitory activity vary considerably from brand-to-brand, but are consistent within each brand. While most have inhibitory activity to both MAO A and MAO B, samples of tequila from certain specific manufacturers inhibited only MAO B activity. Certain other agave derived products were found to inhibit only MAO A activity.

An important aspect of the agave derived MAO inhibitors for their use in food or drink products is that they are reversible rather than irreversible inhibitors, as demonstrated in Example 1 below. Irreversible MAO inhibitors are pharmaceutical products now in limited use due to this mechanism of action that permanently neutralizes the target protein. Tequila consumption is not known to be associated with the characteristic side effects of irreversible inhibitors, such as serotonin syndrome (excess MAO B inhibition) or "the cheese effect" (excess MAO A inhibition). The uncontrolled (by medical supervision) amounts of composition consumed when included in food or drink mandates the property of reversibility.

The compositions prepared by the improved methods may be used as a food supplement and/or included in foods or medicines, or used to treat depression, Parkinson's disease or general malaise, and may also be used as an adjunct or substitute for coffee or in decaffeinated products. The compositions may be mixed with one or more carriers, excipients and/or diluents that are pharmaceutically or nutritionally acceptable. Thus, in general, the compositions may be included in juices or other soft drinks such as colas or fruit flavored sodas, or can be consumed directly. The compositions may also be included in foodstuffs such as uncooked liquids, for example salad dressings, and consumed along with the solid components of the salad. The amounts of compositions to be consumed or administered to subjects is highly dependent on the nature of the condition to be treated as well as the concentrations of the MAO inhibitors determined to be in the composition itself. Levels of MAO inhibitors useful for various medical indications are known in the art and these guidelines can be followed. For use as food supplements, this is a matter of the judgment of the nutritionist or other practitioner.

The subjects to be treated are generally human, but other mammals such as livestock and companion animals may also benefit. Thus the compositions obtained by the improved methods of the invention may be used in pharmaceutical and veterinary compositions. Laboratory models, such as murine models, may also be used as subjects.

In the embodiment wherein RO is used, commercial water purification systems, such as (Osmonics E2/EZ2 Series, GE water) can be modified to separate MAO inhibitors from ethanol in fermented agave plant sources and is illustrated below. Brass components may be replaced with stainless steel and the flow path altered and electronic flow control components removed. The modified RO system separates the agave derived MAO inhibitors from ethanol while operating at low pressure, which has the advantage of requiring less energy than conventional alcohol removal RO systems. The osmotic pressure of a solution is directly related to the concentration of solute and in order for a reverse osmosis system to function, the pressure across the membrane must be higher than the osmotic pressure of the solution.

The unmodified GE Water system shown in FIG. 1 is capable of processing brackish water at an operating range of 165-250 psi across the membrane, which is considered low pressure compared to systems running at 1000-2000 psi used to process sea water. Low pressure water purification systems such as the GE Water unit require a feed supply (1) delivered to the RO pump (2) at a minimum pressure equivalent to that found in a municipal water supply (30-50 psi). The RO pump boosts the pressure of the feed to supply the membrane (3), water migrating across the membrane (permeate) (4) is normally captured for drinking while solution not passing through the membrane (concentrate) (5) is discarded.

In the present invention, the flow path of the conventional system was altered to redirect the concentrate from the membrane to the feed supply.

In the Examples below, specific illustrations of the improvements in the method to obtain compositions substantially free of alcohol that nevertheless contain the volatile inhibitors of monoamine oxidase are shown. These are not limiting, but illustrative. In some cases, an extra pump is added to adjust suitable pressure in addition to the single pump generally supplied with a reverse osmosis apparatus that is commercially available. A gauge and/or valves may also be included. In addition, these systems are redesigned as to recycle the concentrate from each pass through the membrane into a reservoir so that the concentrate remaining in the reservoir is lower in alcohol percentage but contains the desired inhibitors. In some instances, the level of liquid contained in the reservoir is maintained at a desired level. In other instances, additional water is supplied immediately upstream of the membrane. Generally, the distilled agave ferment is diluted prior to the reverse osmosis process.

Other procedures include harvesting the inhibitors under reduced pressure as demonstrated below and one further example demonstrates that the method of the invention may be applicable to distillates obtained from fermented pulque as it is demonstrated that fermented agave species that result in pulque also contain the desired inhibitors. Distillates of pulque are not commercially available for reasons not related to the applicability of the invention.

The following materials and procedures were used in the examples below:

Assay for Ethanol

The ethanol assay was from Analytical Biochemistry 132, 418-423 (1983). A master mix containing per 100 assays:

13.7 ml distilled water 18 ml 0.6M tris/0.4M lysine buffer 2 ml 28 mM NAD (N6522 Sigma)

0.5 ml alcohol dehydrogenase (5.4 mg/ml)—added immediately before adding to wells An optical density plate reader and compatible 96-well clear plates are used for this assay. To each well, 342 µl of master mix is first added, then 18 µl of each standard and samples at 200 and 400-fold dilutions. The standard curve is constructed by diluting 100% ethanol 5000-fold and serially diluting fs, 1:2, 1:4, 1:8. The plate is incubated at room temperature for 4-10 minutes and read in the plate reader at OD340 nm.

Assay for MAO Action

The MAO assay was from Bioorganic & Medicinal Chemistry 13 (2005) 6212-6217. A master mix containing per 100 assays:

2 ml distilled water 4.8 ml potassium phosphate buffer (0.1 M, pH 7.4, made isotonic with KCl)

0.3 ml 0.75 mM kynuramine dihydrobromide

Recombinant MAO A and B are from Corning. The proteins are thawed and aliquoted 20 µl per tube and refrozen at −80° C. For the assays, a tube of each protein is removed from the freezer and 580 µl of buffer is added, then 9 µl is added to each assay.

A black fluorescence compatible plate is used and 20 µl of sample is to each well, then 71 µl of master mix is added followed by 9 µl of MAO recombinant protein. The plate is sealed and placed in an incubator at 37° C. for 30 minutes. After incubation, the sealer is removed and 50 µl of 2N NaOH is added. The plate is read at excitation 320/405 emission in a fluorescence spectrophotometer.

Example 1

Reversibility of MAO Inhibitors from Agave Distillates

Tequila samples were assayed for MAO inhibitory activity with or without pre-incubation at 37° C. for 20 minutes with recombinant MAO A or B. Kynuramine substrate was then added to all assays before 30 minute incubation at 37° C. according to the assay protocol.

Reversible inhibitors show no change in inhibitory activity with pre-incubation with the proteins as seen in Table 1. Irreversible inhibitors show increased inhibition with pre-incubation due to chemical interaction between the compound and protein.

TABLE 1

| | Pre-Incubation | | No Pre-Incubation | |
|---|---|---|---|---|
| | % Inhibition MAO A | % Inhibition MAO B | % Inhibition MAO A | % Inhibition MAO B |
| Tequila 1 | 8 | 23 | 7 | 31 |
| Tequila 2 | 19 | 30 | 18 | 37 |

Example 2

Figure 2:
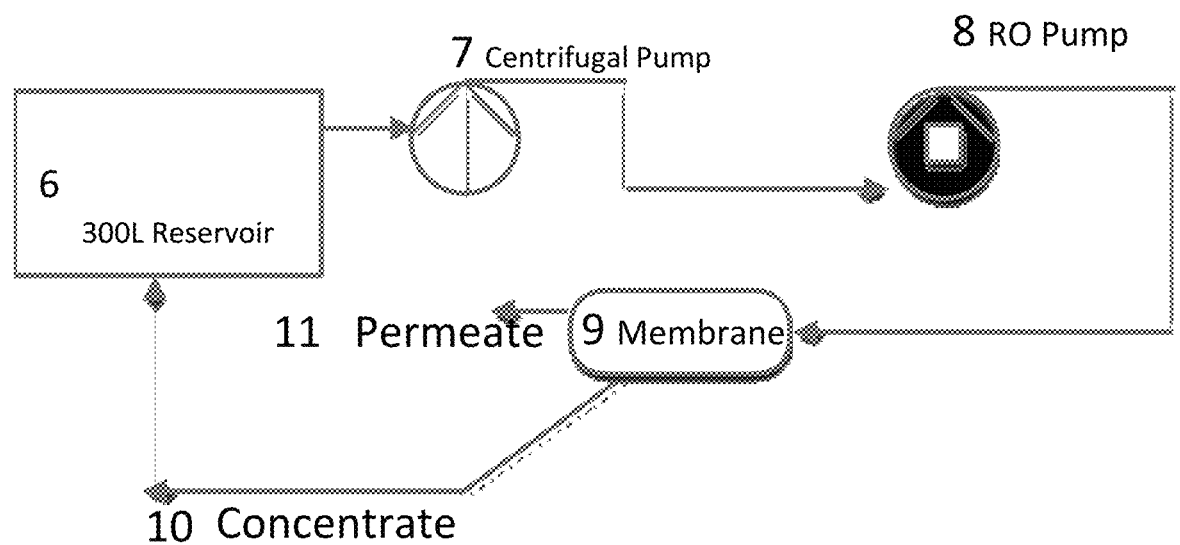
FIG. 2 shows a modified reverse osmosis system of the invention which includes an additional pump to adjust the pressure and recycles the concentrate of the membrane into the reservoir.

A modified RO system is shown in FIG. 2. In this system 3 L of Kirkland anejo tequila was diluted with distilled water to a volume of 300 L in a reservoir (6) connected to a centrifugal pump (7) (HP75SS-425-21211-100-36-1T6, Price Pumps). The centrifugal pump supplied the RO pump (8) with the diluted tequila feed at 40 psi and the RO pump boosted the feed supply pressure to the membrane (9). After exiting the membrane housing, the concentrate (10) was channeled back to the reservoir to be continuously recycled while the permeate flow (11) (ethanol and water) was discarded after analysis. Pressure across the membrane was adjusted by a valve restricting the concentrate flow and the pressure was monitored by a gauge installed between the membrane and the valve. The volume of concentrate decreased with continuous recycling at a pressure of 220 psi across the membrane while the concentration of MAO inhibitors and ethanol increased relative to the 100-fold dilution. The machine was run until the volume of concentrate equaled the original 3 L volume.

The strategy behind this RO hardware configuration and operational protocol was successful in separating MAO inhibitor compounds from ethanol, but required an initial 100-fold dilution of tequila and produced 1.8% ABV concentrate, much higher than the desired 0.4% ABV. Presumably, the limit to ethanol reduction is related to osmotic pressure of the concentrate and low operating pressure of the system. During the 300 L-to-3 L volume reduction run of the machine, fifteen containers at 19 L each of permeate was collected and ethanol assays were run on containers 1, 5, 11 and 15. The results are shown in Table 2.

Example 3

Figure 3:
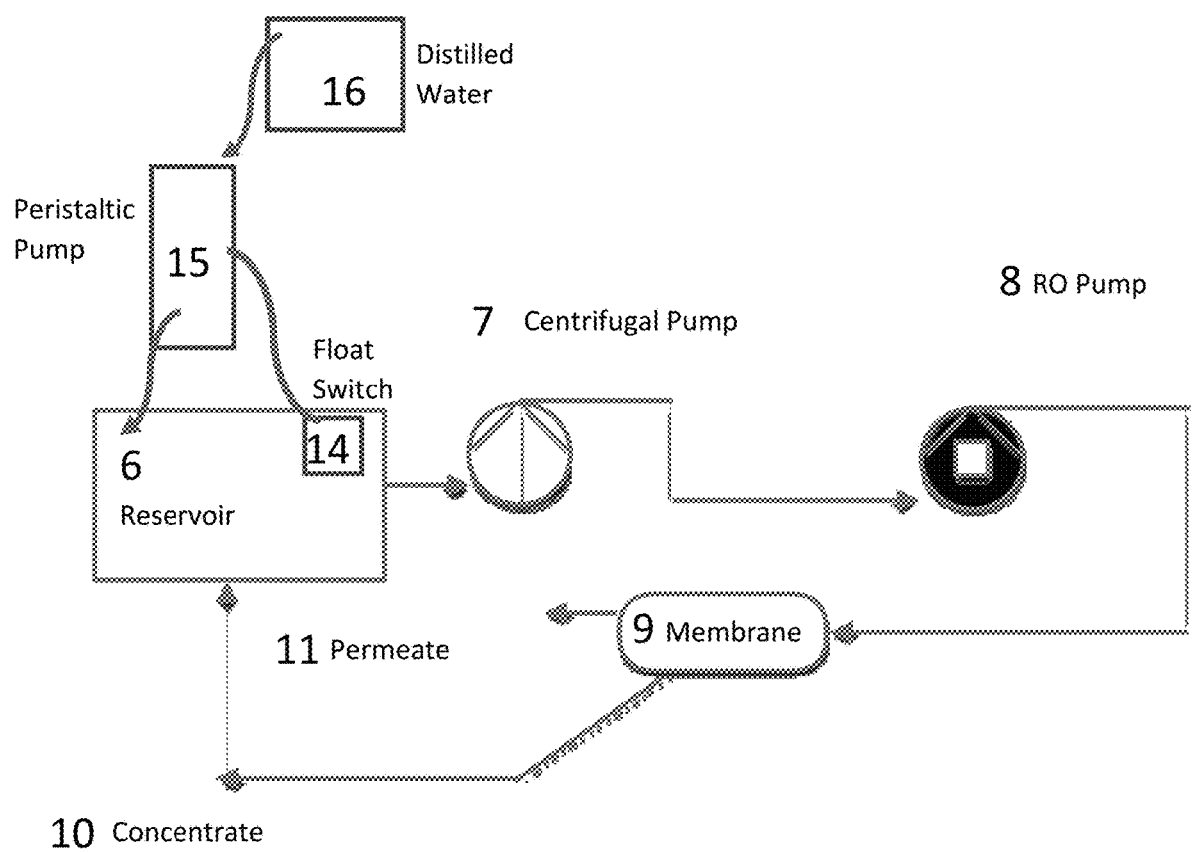
FIG. 3 shows a further modification of the system of FIG. 2 which maintains the volume of liquid in the reservoir.

An additional improved RO system is shown in FIG. 3. In this system, 3 L of Kirkland anejo tequila was diluted to 30 L in a 40 L reservoir (6) fitted with a float switch (14) (Omega Engineering, LVK-130×2; solid state relay SSRL2) connected to a peristaltic pump (15) (Cole Parmer). The float switch was adjusted to maintain a volume of 30 L in the reservoir by energizing the peristaltic pump to deliver distilled water (16) when the level in the reservoir fell below 30 L. MAO inhibitors were separated from ethanol with this method and the ethanol concentration was significantly lower in the final concentrate compared to Example 2. Fifteen containers at 19 L each of permeate was collected and ethanol assays were run on all containers. Results for containers 1, 5, 11 and 15 are shown in table 2.

This strategy was successful in separating MAO inhibitor compounds from ethanol at low system pressure using a 10-fold initial dilution of tequila producing 0.1% ABV concentrate after processing 285 L of distilled water. This method was a significant improvement over Example 1 since the ethanol concentration was even lower than the 1:100 dilution of tequila.

Example 4

Figure 4:
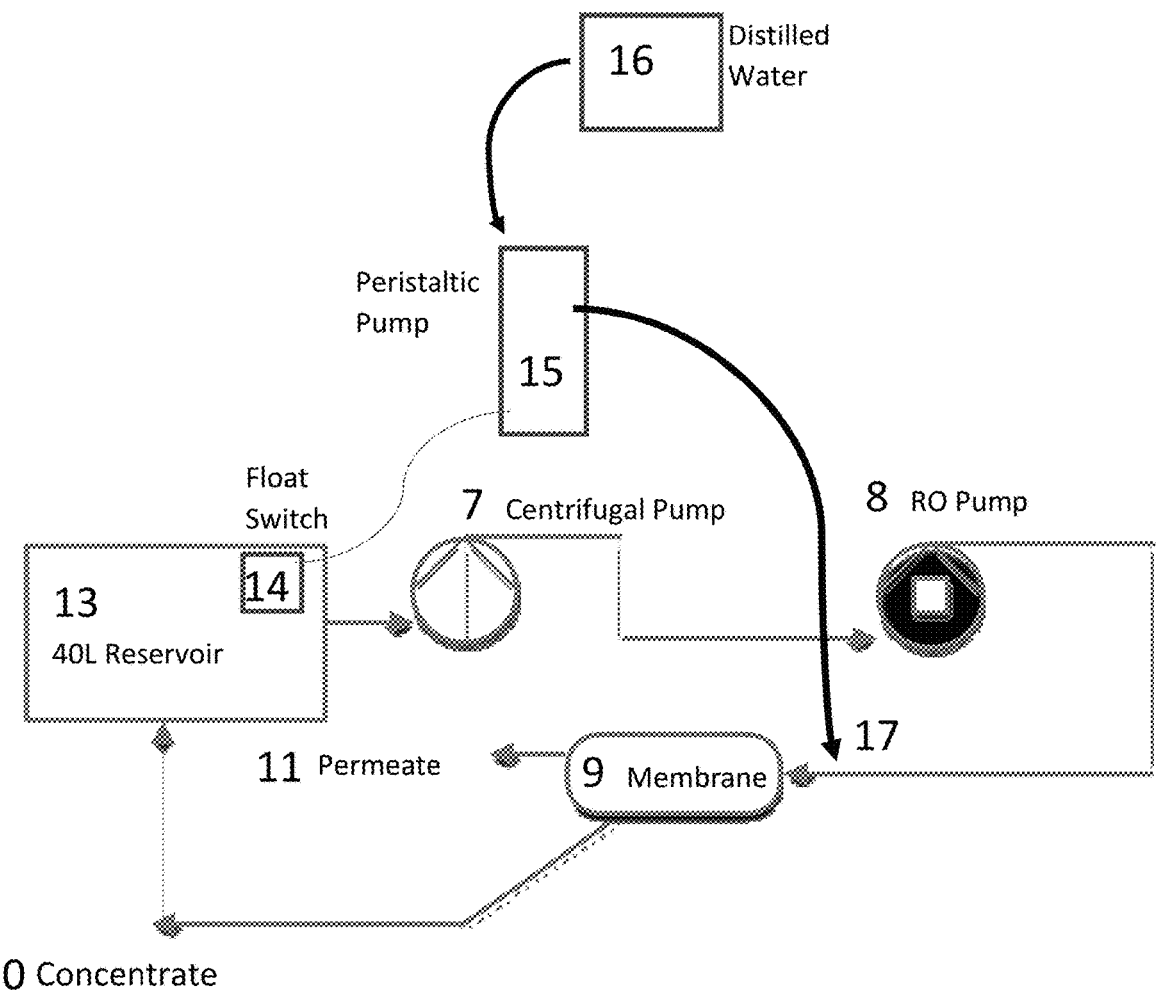
FIG. 4 shows still another modification of the system of FIG. 2 wherein the distilled water from the peristaltic pump is provided upstream of the membrane.

Another method of production is shown in FIG. 4. The system was configured as in Example 3 except that distilled water was introduced immediately before the membrane by the peristaltic pump at arrow (17) instead of at the reservoir. MAO inhibitors were also successfully separated from ethanol with this method and the ethanol concentration was significantly lower in the final concentrate compared to Example 2, but the ethanol concentration was not as low as Example 3. In this method, 228 L of water was used rather than 285 L as in Example 3 during the processing. Each container of permeate was collected and ethanol assays were run on all containers. Results for containers 1, 5, 11 and 15 are shown in table 2.

This strategy was successful in separating MAO inhibitor compounds from ethanol at low system pressure using a 10-fold initial dilution of tequila producing 0.4% ABV concentrate after processing 228 L of distilled water.

TABLE 2

MAO inhibition and Ethanol Concentration associated with RO methods of Examples 2-4

| | | % Inhibition | | % Ethanol |
|---|---|---|---|---|
| | | MAO A | MAO B | by Volume |
| Example 2 | 1:10 Dilution KA pre-RO | 13 | 44 | 3.8 |
| | 1:100 Dilution KA pre-RO | 0 | 11 | 0.7 |

TABLE 2-continued

MAO inhibition and Ethanol Concentration associated with RO methods of Examples 2-4

|  |  | % Inhibition | | % Ethanol |
|---|---|---|---|---|
|  |  | MAO A | MAO B | by Volume |
|  | RO Concentrate | 33 | 70 | 1.8 |
|  | RO Permeate 1 | — | — | 0.4 |
|  | RO Permeate 5 | — | — | 0.4 |
|  | RO Permeate 11 | — | — | 0.5 |
|  | RO Permeate 15 | — | — | 0.8 |
| Example 3 | 1:10 Dilution KA pre-RO | 7 | 38 | 3.9 |
|  | RO 3L Final Concentrate | 24 | 63 | 0.1 |
|  | RO Permeate 1 | — | — | 2 |
|  | RO Permeate 5 | — | — | 0.4 |
|  | RO Permeate 11 | — | — | 0.1 |
|  | RO Permeate 15 | — | — | 0.01 |
| Example 4 | 1:10 Dilution KA pre-RO | 7 | 29 | 3.5 |
|  | RO Concentrate | 25 | 64 | 0.4 |
|  | RO Permeate 1 | — | — | 1.6 |
|  | RO Permeate 5 | — | — | 0.46 |
|  | RO Permeate 11 | — | — | 0.13 |
|  | Clorgyline | 97 |  |  |
|  | Parglyine |  | 86 |  |

Example 5

Isolation of Agave Derived MAO Inhibitors Under Reduced Pressure

The inhibitors are volatile compounds that typically co-evaporate with ethanol, but may be separated from ethanol under conditions of reduced pressure according to the following procedure:

A 1.6 ml polypropylene microfuge tube containing 1 ml of anejo tequila (40% ABV), was placed in a centrifugal vacuum concentrator (Savant Speed Vac) under a vacuum of 200 Torr at 40° C. for 30 minutes, which conditions resulted in a final volume of 750 µl. Using an enzymatic assay, the ethanol concentration was measured at 16% ABV and dilutions of the concentrated sample and tequila were assayed for MAO A and B inhibitors. The 25-fold diluted tequila sample (1.6% ABV) shows 0% inhibition of MAO A activity and 8% inhibition of MAO B activity and the 10-fold concentrated sample (1.6% ABV) shows 52% inhibition of MAO A and 79% inhibition of MAO B. This demonstrates that the MAO inhibitors can be separated from ethanol under reduced pressure.

This method of separation of MAO inhibitors from ethanol in fermented agave sources illustrates proof of concept for the successful commercial production using spinning cone column (SCC) or pervaporation techniques of ethanol removal. Conditions would be adjusted to maximize the desired results as in ratio of MAO inhibitors for the final product because the inhibitors are volatile compounds that may be selectively isolated from ethanol depending upon vacuum/temperature.

Example 6

Agave Species Producing MAO Inhibitors Other than Blue Weber Agave

Agave derived MAO inhibitors are also found in the fermentation products of aguamiel (honey water) produced from the maguey plant or Americana agave. The fermented beverage from aguamiel is known as pulque and may be produced from agave other than Blue Weber agave, which is restricted for the production of tequila. For pulque production the maguey plant sap is harvested and fermented immediately since the sap contains simple fermentable sugars. Reports of microorganisms include thermo bacteria (which produce ethanol) in addition to yeasts.

The MAO inhibitors are separated from ethanol by one the methods described above after first filtering solid material from the fermentation mash. To evaluate MAO inhibitory activity in the fermented source, pulque was purchased from a commercial supplier (Hacienda 1881) as a canned, pasteurized beverage (5.4% ABV). Inhibitory activity to MAO A and B from Pulque and Kirkland Anejo tequila each diluted to 1.35% ABV for the MAO assay was determined. Tequila shows 5% inhibition of MAO A and pulque shows 8% inhibition. MAO B activity is inhibited by tequila and pulque at 22% and 30%, respectively. These results demonstrate the potential to produce agave derived inhibitors from sources other than Blue Weber Agave, which according to international law is restricted to tequila production and grown only in Mexico. The Americana agave is found in many parts of the southwest USA as well as other regions.

The invention claimed is:

1. A method to obtain an improved composition of monoamine oxidase (MAO) A and/or monoamine oxidase (MAO) B inhibitors from a distillate of fermented agave extract of by reverse osmosis which method comprises diluting the distillate in a feed reservoir of a reverse osmosis system and recycling said diluted distillate across a separation membrane to obtain a permeate and a concentrate that is returned to the feed reservoir at each cycle; and
   continuing to recycle each successive concentrate to obtain a final concentrate that contains less than 1.5% alcohol by volume (ABV), thus obtaining an improved composition of said inhibitors.

2. The method of claim 1 which further includes diluting the recycled concentrates with distilled water immediately prior to recycling the said concentrates past the membrane.

3. The method of claim 1 which further includes diluting the recycled concentrates in said feed reservoir with distilled water.

4. The method of claim 1 wherein the reverse osmosis system contains at least two pumps to enhance pressure at the membrane.

5. The method of claim 1 wherein the membrane has a cutoff of approximately 100 Daltons molecular weight.

* * * * *